(12) United States Patent
Boonefaes

(10) Patent No.: US 10,126,233 B2
(45) Date of Patent: Nov. 13, 2018

(54) DNA AND/OR RNA DETERMINATION FROM UV-VIS SPECTROPHOTOMETER DATA

(75) Inventor: Tom Boonefaes, Ghent (BE)

(73) Assignee: UNCHAINED LABS, Pleasanton, CA (US)

( * ) Notice: Subject to any disclaimer, the term of this patent is extended or adjusted under 35 U.S.C. 154(b) by 439 days.

(21) Appl. No.: 14/002,685

(22) PCT Filed: Feb. 29, 2012

(86) PCT No.: PCT/EP2012/053481
§ 371 (c)(1),
(2), (4) Date: Aug. 30, 2013

(87) PCT Pub. No.: WO2012/117036
PCT Pub. Date: Sep. 7, 2012

(65) Prior Publication Data
US 2013/0332084 A1 Dec. 12, 2013

Related U.S. Application Data

(60) Provisional application No. 61/447,941, filed on Mar. 1, 2011.

(30) Foreign Application Priority Data

May 29, 2011 (EP) .................................. 11168005
Jan. 3, 2012 (GB) .................................. 1200031.1

(51) Int. Cl.
*G01N 21/33* (2006.01)

(52) U.S. Cl.
CPC ..... *G01N 21/33* (2013.01); *G01N 2201/1293* (2013.01)

(58) Field of Classification Search
None
See application file for complete search history.

(56) References Cited

U.S. PATENT DOCUMENTS 7,786,295 B2 8/2010 Heath et al.

FOREIGN PATENT DOCUMENTS

| EP | 1524514 A1 | 4/2005 |
|---|---|---|
| EP | 2 495 546 A1 | 9/2012 |
| EP | 2681532 A1 | 1/2014 |
| JP | 2007116995 A | 5/2007 |
| WO | WO-2012/117036 A1 | 9/2012 |

OTHER PUBLICATIONS

Rachmayanti, "Isolation of DNA from unprocessed and processed wood of Dipterocarpaceae," Diss. Georg-August University of Göttingen, 43 pages, 2009.*
Tataurov, "Predicting ultraviolet spectrum of single stranded and double stranded deoxyribonucleic acids," Biophysical chemistry, vol. 133.1, p. 66-70, 2008.*
International Search Report from corresponding PCT Application Serial No. PCT/EP2012/053481, dated Jun. 28, 2012.
A. de Juan et al., "Chemometrics Applied to Unravel Multicomponent Processes and Mixtures Revisiting Latest Trends in Multivariate Resolution", Chemometrics Group, Universitat de Barcelona, Barcelona, Spain, Jun. 4, 2003, Elsevier, Analytica Chimica Acta 500 (2003), pp. 195-210.
M. Garrido et al., "Multivariate Curve Resolution-Alternating Least Squares (MCR-ALS) Applied to Spectroscopic Data From Monitoring Chemical Reactions Processes", Anal Bioanal Chem (2008) 390:2059-2066; Mar. 5, 2008.
J. Jaumot et al., "Resolution of Parallel and Antiparallel Oligonucleotide Triple Helices Formation and Melting Processes by Multivariate Curve Resolution", Journal of Biomolecular Structure & Dynamics, ISSN 0739-1102, vol. 21, Issue 2, Jun. 13, 2003.
Javier Saurina, et al., "Procedure for the Quantitative Determination of Mixtures of Nucleic Acid Components Based on Multivariate Spectrophotometric Acid-Base Titrations", Analytical Chemistry, vol. 71, No. 1, Jan. 1, 1999.
Dirk W. Lachenmeier et al., "Multivariate Curve Resolution of Spectrophotometric Data for the Determination of Artificial Food Colors", Journal of Agricultural and Food Chemistry, vol. 56, No. 14, 2008.
T. Azzouz et al., "Application of Multivariate Curve Resolution Alternating Least Squares (MCR-ALS) to the Quantitative Analysis of Pharmaceutical and Agricultural Samples", Elsevier, Talanta 74 (2008), p. 1201-1210, Aug. 30, 2007.
European Search Report from EP Application No. EP11168005, dated Aug. 23, 2011.
Kessler et al., "Multivariate Curve Resolution-Integration von Wissen in Chemometrische Modelle", Chemie Ingenieur Technik, vol. 82, Issue 4, Apr. 2010.

(Continued)

*Primary Examiner* — G Steven Vanni
(74) *Attorney, Agent, or Firm* — Cooley LLP

(57) ABSTRACT

A method for analyzing UV-VIS spectrophotometer data of a sample comprising at DNA and/or RNA is described. The method comprises receiving UV-VIS spectrophotometer data, fitting the UV-VIS spectrometer data taking into account at least one spectrum representative for a base pair being any of more of adenine-thymine (AT) or guanine-cytosine (GC) or adenine-uracil, and deriving from the fitting a quantification of an amount of DNA and/or RNA.

18 Claims, 10 Drawing Sheets

(56) References Cited

OTHER PUBLICATIONS

Spjotvol et al., "Restricted Least Squares Estimation of the Spectra and Concentration of Two Unknown Constituents Available in Mixtures", Technometrics, vol. 24, No. 3, Aug. 1982, 9 Pages.
"Product Information Sheet for Calf Thymus DNA" http://www.sigmaaldrich.com/content/dam/sigmaaldrich/docs/sigma/product_information_sheet/d8661pis.pdf. Retrieved Sep. 29, 2015.
Mach H. et al. "Detection of Proteins and Phenol in DNA Samples with Second-Derivative Absorption Spectroscopy", Analytical Biochemistry, vol. 200, No. 1, 1992, pp. 20-26.
Owen T., "Fundamentals of Modern UV-Visible Spectroscopy", Agilent Technologies, Publication No. 5980-1397E, Jun. 2000.
U.S. Appl. No. 61/447,941, filed Mar. 1, 2011.
European Patent Application No. 11168005.4, Filed May 29, 2011.
Great Britain Patent Application No. 1200031.1, Filed Jan. 3, 2012.
Screenshots of Product Information for DNA from Calf Thymus, "High Polymerized", http://www.sigmaaldrich.com/catalog/product/sigma/d1501?lang=de&region=DE., Retrieved on Dec. 7, 2015.
Montoye T. Application Note 1.6, "Specific RNA quantification using cDrop: Comparison with UV Absorbance, the Ribogreen Fluorescent assay and the Agilent Bioanalyser", Jul. 2011, http://www.trinean.com/sites/default/files/generated/files/documents/an_1.6_specific_ma_quantification.pdf. Retrieved on Aug. 28, 2015.
Montoye T. et al. Application Note 1.5, "Specific dsDNA Quantification—UV/VIS-based cDrop Method vs Picogreen Fluorescent Assay", 2011, http://www.trinean.com/sites/default/files/generated/files/documents/an_1.5_specific_dsdna_quantification_cdrop_vs_picogreen_fluorescent_assay.pdf. Retrieved on Aug. 28, 2015.
Montoye T. et al. Application Note 1.4, "Specific dsDNA Quantification—a Comparative Test Between the UV/VIS-based cDrop Method and Picogreen Fluorescent Assay", May 2011, http://www.bmskorea.co.kr/bms_email/11-0614/trinean.pdf. Retrieved on Aug. 28, 2015.
Barbas, C.F. et al. (2007). "Quantification of DNA and RNA," Cold Spring Harbor Protocols, located at http://cshprotocols.cshlp.org/content/2007/11/pdb.ip47.full.
Condit, R.C. (2007). Fields "Principles of Virology," vol. 1, Chapter 2, 5$^{th}$ edition, Lippincott-Raven Publishers.
Esbensen, K.H. (2009). Multivariate data analysis in practice: An Introduction to multivariate data analysis and experimental design, 5$^{th}$ edition, p. 118.
Gonen, Y. et al. (2009). "Using a Matlab implemented algorithm for UV-vis spectral resolution for p$k_a$ determination and multicomponent analysis," *Analytical Chem. Insights* 4:21-27.
Integrated DNA Technologies (2016). "Oligo quantification—getting it right," located at http://www.idtdna.com/pages/education/decoded/article/oligo-quantification-getting-it-right, 4 total pages.
Marquet, R. et al. (1988). "Determination of the A-T content of DNA by second-derivative ultraviolet spectroscopy," *Analytical Biochem.* 176:265-268.
Martens, H. et al. (1989). "Multivariate calibration," pp. 70-71.
Schleifer, A. et al. (1980). "A task-oriented approach to spectrophotometry," Hewlett-Packard J. 31:11-17.
Ulitzur, S. (1972). "Rapid determination of DNA base composition by ultraviolet spectroscopy," *Biochimica at Biophysica Acta* 272:1-11.

\* cited by examiner

DNA AND/OR RNA DETERMINATION FROM UV-VIS SPECTROPHOTOMETER DATA

FIELD OF THE INVENTION

The invention relates to the field of sample characterisation. More particularly, the present invention relates to methods and systems for analyzing samples using recorded spectra, such as for example for analyzing samples comprising DNA and/or RNA.

BACKGROUND OF THE INVENTION

Although numerous analysis techniques for qualification and quantification of samples exists, only few analysis techniques are as simple to perform, fast and accurate as spectrophotometry. One example of spectrophotometry is UV-VIS absorbance spectroscopy. During such experiments, samples are irradiated with UV-VIS radiation of different wavelengths, the radiation remaining after passage through the sample is detected and the absorbance at different wavelengths is determined. As particular components will show a particular absorbance at particular wavelengths, such a particular absorbance profile can be used as a fingerprint which allows, upon comparison with reference spectra, to identify the components. When more complex samples are studied, the absorbance features in the spectrum can be more broad, rendering the interpretation of spectra substantially more difficult.

A number of different spectral analysis techniques have been described in the past.

Some methods are provided allowing determining the concentration or relative concentration of components of a sample based on the approximation of the measured spectrum with a linear combination of standard, also referred to as reference, spectra of the individual components. Approximation of the measured spectrum with reference spectra may be performed using minimization techniques for fitting the reference spectra to the absorption spectra, such as for example least squares regression or least absolute deviations regression. Such methods also may be iteratively applied.

More complex methods also are known, such as methods making use of derivatives of a spectrum, as amongst others the latter may allow to increase the insensitivity to wavelength shifts. One example of a method using derivatives is the analysis of a protein mixture using the second derivative spectrum of the sample. Another known method is based on matrix computation for determining the concentration of a number of chemical components using a number of predetermined spectral data of each chemical component, whereby the number of predetermined spectral data is larger than the number of chemical components to be determined. Some of the known methods are based on cross-correlation of samples and reference spectra, both being weighted by mean transmittance per wavelength. Particular applications for analyzing samples with known composition have been described, such as for example analysis of the composition of a protein using electromagnetic spectroscopy, analysis of RNA wherein samples are chemically split in AC and GU fractions and the AC and GU composition is then determined based on absorption at 260 nm.

Furthermore, also some methods are known that deal with unknown component spectra. Methods are known wherein the separation of unknown component spectra from samples is based on constrained linear or quadratic programming and sample transforms, i.e. wavelet transforms. Other methods make use of approximated component spectra by point-wise cross-correlation of absorbance and making use of known concentration. Several techniques make use of principal component analysis (PCA) for obtaining diagnostically relevant reference spectra from a database of spectra associated with disease states whereby correlation with reference spectra is used to aid in the diagnosis of a new sample.

Spjotvoll et al. describe in Technometrics 24 (1982) a technique for determining spectra and concentrations of two-constituent mixtures based on a least squares estimator. A method is discussed for identification of two unknown chemical compounds and an estimation of their proportion in a set of unknown mixtures of the two compounds. It is based on a least-squares fit and principle component analysis for separation whereby additional constraints are introduced such as the sum of concentrations being equal to unity and spectra and concentrations being non-negative.

The use of UV-VIS spectrophotometer data for DNA and/or RNA quantification or analysis still has not found its breakthrough due to the lack of an accurate and efficient analysis technique for the obtained results.

Therefore, there is need for a method allowing analysis of samples comprising DNA and/or RNA components, particularly using UV-VIS spectroscopy.

SUMMARY OF THE INVENTION

It is an object of embodiments of the present invention to provide good methods and systems for analyzing UV-VIS spectroscopy spectra of samples and good corresponding methods and systems for characterizing samples comprising DNA and/or RNA. The sample advantageously comprises double stranded DNA, although the technique also can be used for samples comprising only RNA. The UV-VIS spectroscopy spectra may be UV-VIS absorbance spectra.

It is an advantage of embodiments according to the present invention that systems and methods are provided allowing to assist in PCR analysis, e.g. without the need for purifying the reaction mixture, even if the reaction mixture is a mixture of 4dNTP's, primer oligo's, polymerase-enzyme and DNA in the sample.

It is an advantage that methods and systems according to embodiments of the present invention allow for obtaining relevant and conclusive results.

The above objective is accomplished by a method and device according to the present invention.

The present invention relates to a computer-implemented method for analyzing UV-VIS spectrophotometer data of a sample comprising at least DNA and/or RNA, the at least DNA and/or RNA advantageously being at least double stranded DNA, the method comprising receiving UV-VIS spectrophotometer data, fitting the UV-VIS spectrometer data taking into account at least one spectrum representative for a base pair being any of adenine-thymine (AT) or guanine-cytosine (GC) or adenine-uracil (AU), and deriving from the fitting a quantification of an amount of DNA and/or RNA, the deriving being advantageously deriving from the fitting a quantification of an amount of double stranded DNA. It is an advantage of embodiments of the present invention that UV-VIS spectrophotometer data can be used for characterizing, without a lot of prior knowledge, a DNA and/or RNA containing sample. Quantification may be quantification of an amount of double stranded DNA (dsDNA).

Said fitting may comprise taking into account a set of reference spectra representative for two distinct base pair contents. The spectra representative for distinct base pair contents may be representative for base pair contents differing at least 20%, advantageously at least 30%, more advantageously at least 40%, e.g. at least 50%.

Said fitting may comprise taking into account a set of two reference spectra representative of two distinct GC contents.

Said fitting may comprise taking into account a set of exactly two reference spectra representative for two distinct GC contents.

Said fitting may comprise fitting UV-VIS spectrophotometer data of a sample comprising DNA and/or RNA having at least 50 base pairs, advantageously at least 100 base pairs. It is an advantage according to embodiments of the present invention that a fit can be obtained using a restricted number of reference spectra for base pairs, resulting in accurate and efficient fitting.

The sample may comprise DNA and the fitting may comprise using a combination of a set of reference spectra representative for base pairs and reference spectra being representative for separate nucleobases.

Said fitting using a combination of reference spectra representative for base pairs and reference spectra being representative for separate nucleobases may comprise fitting using spectra being the difference spectra between reference spectra representative for base pairs and reference spectra being representative for separate nucleobases. It is an advantage of embodiments according to the present invention that for the analysis of a DNA comprising sample, the AT and GC balance is automatically taken into account. It is an advantage of embodiments of the present invention that only the formed double stranded DNA is quantified and not a mixture of the dsDNA and the formed amplicons, which may occur e.g. in PCR.

The difference spectra between reference spectra representative for base pairs and reference spectra being representative for separate nucleobases may be spectra obtained by subtracting from a given reference spectrum representative for a given base pair, the reference spectra being representative for the corresponding separate nucleobases.

The set of spectra representative for base pairs may consist of two reference spectra representative for samples having two distinct, e.g. two extreme, GC contents.

The reference spectra representative of separate nucleobases may be reference spectra for adenine, guanine, thymine, cytosine and/or uracil.

The method may be adapted for analyzing a PCR reaction of a sample comprising DNA, whereby the deriving may comprise determining an amount of double stranded DNA formed during or after a PCR reaction. It is an advantage of embodiments according to the present invention that analysis can be done of a PCR reaction of a DNA-comprising-sample using UV-VIS spectrometry, without the need for first purifying the reaction mixture formed during the PCR reaction.

Fitting furthermore may comprise taking into account a spectral component for a contamination component.

Taking into account a spectral component for a contamination component may comprise taking into account a spectral component e.g. for one or more of trimethylglycine, guanidinethiocyanate, phenol, ethylenediaminetetraacetic acid, proteins or hemoglobine. It is an advantage of embodiments according to the present invention that compensation for one of the most important contaminants in the PCR reaction can be obtained.

Fitting UV-VIS spectrophotometer data of a sample may comprise fitting UV-VIS spectrophotometer data of a mixture comprising deoxynucleotide Triphosphates, primer-oligo's and polymerase and DNA. It is an advantage of embodiments according to the present invention that the UV-VIS spectrophotometer data directly recorded on the PCR starting mixture can be used, although it has a high optical density value at 260 nm, thus avoiding the need for processing, e.g. purifying, the PCR starting mixture before characterisation.

Fitting furthermore may comprise taking into account one or more spectral components representative for scattering in the sample.

Fitting furthermore may comprise taking into account one or more spectral components representative for turbidity in the sample.

The present invention also relates to a computer-implemented system for analyzing UV-VIS spectrophotometer data of one or more samples comprising DNA and/or RNA, advantageously one or more samples comprising at least double stranded DNA, the system comprising an input means for receiving said UV-VIS spectrophotometer data, a processing means programmed for fitting the UV-VIS spectrometer data taking into account at least one spectrum representative for a base pair being any of adenine-thymine (AT) or guanine-cytosine (GC) or adenine-uracil (AU), and deriving from the fitting a quantification of an amount of DNA and/or RNA, advantageously an amount of double stranded DNA, and an output means for outputting a quantification of an amount of DNA and/or RNA, advantageously the amount of double stranded DNA, for the one or more samples under study.

Said processing means may be adapted for performing fitting as described in any of the above mentioned methods.

The present invention also relates to the use of a method as described above for quantifying an amount of DNA and/or RNA.

The present invention furthermore relates to a computer program product for, if implemented on a processing unit, performing a method as described above.

The present invention also relates to a data carrier medium comprising such a computer program product and/or to the transmission thereof over a wide or local area network.

The above described aspect may be part of, may correspond with, may comprise the steps or features of or may make use of the following aspects of the present invention.

The present invention also relates to a method for analyzing UV-VIS spectrophotometer data of one or more samples, the one or more samples consisting of a number of constituents, the method comprising obtaining prior information for the one or more samples regarding their constituents, obtaining UV-VIS spectrophotometer data for the one or more samples, defining a number of overlapping components contributing in the UV-VIS spectrophotometer data, the number of overlapping components comprising one or more components assigned to known constituents of the one or more samples and the number of components comprising one or more components that cannot be assigned to known constituents of the one or more samples, using the prior information for the one or more samples regarding their constituents and using the UV-VIS spectrophotometer data, estimating the constituents composition and the component contributions to the UV-VIS spectrophotometer data for the number of components for the one or more samples by minimizing a residue between the UV-VIS spectrophotometer data and a fit based on said constituent composition and said component contributions, thus obtaining information regarding the one or more components that cannot be assigned to known constituents of the one or more samples. It is an advantage of embodiments according to the present invention that the analysis method allows for accurate detection of contributions to the spectrum that stem from modified constituents, interaction of different constituents or contaminations in the one or more samples.

Estimating the constituents composition and the component contributions to the UV-VIS spectrophotometer data for the number of components for the one or more samples by minimizing a residue between the UV-VIS spectrophotometer data and a fit based on said constituent composition and said component contributions may be performed iteratively until a residue smaller than a predetermined level is obtained. It is an advantage of embodiments according to the present invention that using an iterative method an increased accuracy for the fit and the corresponding constituent composition and component contribution can be obtained.

The method furthermore may comprise cross-checking the prior information based on any or more of the constituents composition, the component contribution or the residue between the UV-VIS spectrophotometer data and the fit. It is an advantage of embodiments that a cross-check regarding the obtained results can be performed using the prior information regarding the one or more samples.

Said prior information may comprise reference contributions in UV-VIS spectrophotometer data for components assigned to known constituents and said estimating the constituents composition and the component contributions may comprise estimating the component contributions to the UV-VIS spectrophotometer for all components based on the reference contributions and determining an estimate for the constituents composition based on minimization of the residue between the UV-VIS spectrophotometer and the fit based on said estimated component contributions to the UV-VIS spectrophotometer data for all components. It is an advantage of embodiments according to the present invention that accurate composition information of the one or more samples can be obtained based on reference spectra of constituents present in the one or more samples, taking into account the presence of unknown contributions in the UV-VIS spectrophotometer data.

Said prior information may comprise constituent composition information for the one or more samples for the known constituents and said estimating the constituents composition and the component contributions may comprise estimating the constituent composition for all constituents based on the prior information on the constituent composition information for the one or more samples for the known constituents, and determining an estimate for the component contribution to the UV-VIS spectrophotometer data based on minimization of the residue between the UV-VIS spectrophotometer data and the fit based on said estimated constituent composition for all constituents. It is an advantage of embodiments according to the present invention that accurate composition information of the one or more samples can be obtained based on reference spectra of constituents present in the one or more samples, taking into account the presence of unknown contributions in the UV-VIS spectrophotometer data.

The constituent composition and the component contributions may be interrelated by a model defining weighing factors for component contributions as function of the constituent composition and wherein determining an estimate for the constituent composition or for the component contribution comprises taking into account the weighing factors. It is an advantage of embodiments according to the present invention that the composition of constituents in the samples can be taken into account.

Analysis may be performed on spectrophotometer data for a plurality of samples, and said iteratively estimating may be performed for those samples having the smallest residue.

The components that cannot be assigned to known constituents of the one or more samples may be representative for any or more of modified constituents, neighbouring effects of different constituents or contaminations in the one or more samples. Another component that advantageously can be taken into account by components that cannot be assigned to known constituents of the one or more samples may be representative for turbidity caused by concentration or aggregation effects. The method may comprise outputting a contribution related to such turbidity. It is an advantage of embodiments of the present invention that good and/or accurate quantification of components in samples showing high turbidity can be obtained, e.g. based on prior knowledge of reference spectra of components in the sample. Another component that advantageously can be taken into account by components that cannot be assigned to known constituents of the one or more samples may be representative for scatter by residual microparticles. Such particles may be non-intentionally present in the sample, such as for example introduced by earlier processing of the sample. In one example, such residual particles may be magnetical micro-particles. The method may comprise outputting a contribution related to such scattering from residual particles. It is an advantage of embodiments of the present invention that good and/or accurate quantification of components in samples comprising residual particles can be obtained, e.g. based on prior knowledge of reference spectra of components in the sample.

The method may comprise using spectrophotometric data of a plurality of samples, wherein the samples comprises at least one sample wherein at least one unknown constituent is present and at least one sample wherein the at least one unknown constituent is absent.

The number of components may be determined by component analysis.

The number of components may be determined based on principal component analysis.

The present invention also relates to a system for analyzing UV-VIS spectrophotometer data of one or more samples, the one or more samples consisting of a number of constituents, the system comprising an input means for obtaining prior information for the one or more samples regarding their constituents and for obtaining UV-VIS spectrophotometer data for the one or more samples, a processing means programmed for defining a number of components contributing in the UV-VIS spectrophotometer data, the number of components comprising one or more components assigned to known constituents of the one or more samples and the number of components comprising one or more components that cannot be assigned to known constituents of the one or more samples, the processing means furthermore being programmed for using the prior information for the one or more samples regarding their constituents and using the UV-VIS spectrophotometer data, estimating the constituents composition and the component contributions to the UV-VIS spectrophotometer data for the number of components for the one or more samples by minimizing a residue between the UV-VIS spectrophotometer data and a fit based on said constituent composition and said component contributions, thus obtaining information regarding the one or more components that cannot be assigned to known constituents of the one or more samples.

The present invention also relates to the use of a method as described above for identifying and/or quantifying contaminants in DNA and/or RNA samples. Said contaminants may be protein contamination. The contaminants may be PCR-inhibiting contaminants.

The present invention also relates to the use of a method as described above for quantifying an amount of double-stranded DNA in a mixture of double-stranded DNA and single-stranded RNA and/or DNA.

The present invention also relates to the use of a method as described above for obtaining the composition of a polynucleotide or protein.

The present invention also relates to the use of a method as described above for quantification of the modification efficiency in a sample.

The present invention also relates to the use of a method as described above for validating a sample composition or constituent thereof.

The present invention also relates to a computer program product for, if implemented on a processing unit, performing a method as described above. It also relates to a data carrier storing the computer program product and transmission of the computer program product over a network.

It is an advantage of embodiments of the present invention that a powerful data analysis of UV-VIS spectroscopy spectra is obtained.

It is an advantage of embodiments according to the present invention that good quantification can be obtained, both for routine applications and more complex applications.

It is an advantage of embodiments according to the present invention that based on prior knowledge in one or more samples, accurate reference spectra can be obtained for components in the sample.

It is an advantage of embodiments according to the present invention that based on prior knowledge of reference spectra of one or more components in the one or more samples, accurate concentration information can be obtained for components in the sample.

It is an advantage that methods and systems according to embodiments of the present invention allow for obtaining relevant and conclusive results.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

Figure 1:
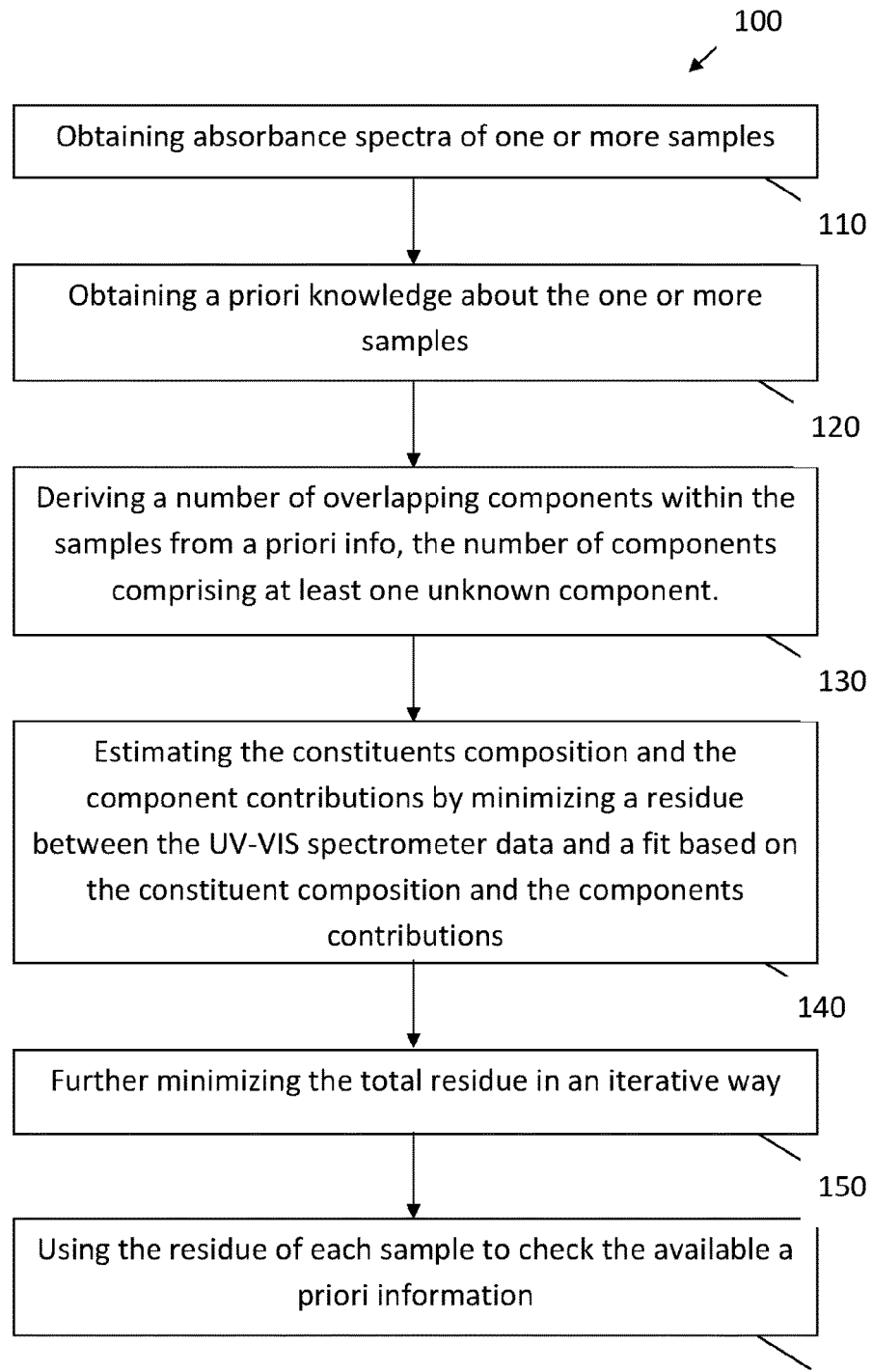
FIG. 1 illustrates a flow chart of a method for analyzing spectra according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Where in embodiments of the present invention reference is made to spectrophotometer data, reference is made to a reflectance, transmittance or absorbance intensity at a given wavelength or as function of wavelength.

Advantageously, the method can be applied to spectrophotometer data being a spectrophotometer spectrum, indicating an intensity as function of wavelength. In advantageous embodiments, the data are absorbance data, representative of the absorption that has occurred in the one or more samples.

Embodiments of the present invention are directed to methods and systems for analyzing UV-VIS spectrophotometer data. Where reference is made to UV-VIS, reference is made to a wavelength region having an upper wavelength in the region 700 nm to 1100 nm and a lower wavelength in the region 150 nm to 300 nm.

Where in embodiments of the present invention reference is made to components contributing to the UV-VIS spectrophotometer data, reference is made to components to an intensity fraction for one or more wavelengths in the spectrophotometer data, e.g. spectrophotometer spectrum. Such a component may be directly assignable to a constituent in the one or more samples or may be not or not directly assignable to a constituent in the one or more samples.

Where in embodiments of the present invention reference is made to components that cannot be assigned to known constituents of the one or more samples, reference is made to components that do not correspond with or for which it is not yet known that these correspond with a physical-chemical absorption characteristic of the constituents of the one or more samples. The components thus do not necessarily correspond to a physical-chemical absorption characteristic of the constituents. The components do not need to correspond with constituents having a significant contribution, e.g. absorbance, within the wavelength region under study. Where in embodiments of the present invention reference is made to constituents of one or more samples, reference is made to biological or non-biological elements such as chemical elements that are present in the sample. Such constituents can for example be one of the following or elements or groups of elements thereof: biopolymers, small organic molecules, metabolites such as glucose or ethanol, proteins, peptides, nucleic acid segments, oligonucleotides, oligonucleotides containing one or more modifications such as for example fluorescent dye labels or chromophores, chemical linker modifications such as aldehyde, phosphate, amine- or thiol-modifications, affinity-labels such as biotin, reactive components such as enzymes (ALP, HRP), alternative bases such as deoxyuracil, deoxyinosine, phosphothiolates, locked nucleic acids, polynucleotides, nucleotides, oligos, peptide nucleic acids, antibodies and variations thereof such as for example nanobodies or alphabodies, micro- and nanoparticles either intentionally or unintentionally added, magnetic or non-magnetic particles, lipids, micelles, vesicles, viral particles, metal-complexes, interacallating dyes and polymers such as polythiophene-derivatives, chromogens such as p-NPP, tetrazolium salts, staining reagents such as Coomassie, methyl blue, eosin, molecules such as small molecule pharmaceuticals, antibiotics or drugs, molecules with a regulatory effect in enzymatic processes such as promoters, activators, inhibitors, or cofactors, viruses, bacteria, cells, cell components, cell membranes, spores, DNA, RNA, micro-organisms and fragments and products. Such constituents also can be for example chemical elements, such as chemical elements present in a pharmaceutical or chemical product.

Where in embodiments according to the present invention reference is made to overlapping components, reference is made to the fact that the component contribution to the spectrum of such components is significant at the same wavelength or in the same wavelength range.

Where in embodiments of the present invention reference is made to turbidity, reference is made to cloudiness or haziness of a fluid caused by individual particles that are generally invisible to the naked eye.

In a first aspect, the present invention relates to a method for analyzing UV-VIS spectrophotometer data of one or more samples. A typical disadvantage of UV-VIS spectrophotometer data of complex data is that different contributions e.g. corresponding with different constituents in the sample or with unknown constituents, will result in overlapping contributions. This results in broad-banded spectra, whereby the different contributions are not as such identifiable from the spectra in the form of shoulders or peaks. Embodiments of the present invention allows analyzing of UV-VIS spectrophotometer data of such complex samples resulting in spectra with broad band absorption built up by overlapping contributions.

Methods according to embodiments of the present invention can be used for analysis of one or more samples. Whereas analysis of a single sample is possible, the method is especially suitable for analyzing spectrophotometer data of multiple samples. The one or more samples comprise a number of constituents. The methods according to embodiments of the present invention are especially suitable for analyzing data for samples having two or more, advantageously three or more constituents. According to embodiments of the present invention, the methods are especially suitable for analyzing UV-VIS spectrophotometer data of a sample comprising at least DNA and/or RNA. The method according to embodiments of the present invention, being a computer-implemented method, comprises receiving UV-VIS spectrophotometer data, fitting the UV-VIS spectrometer data taking into account at least one spectrum representative for a base pair being any of adenine-thymine (AT) or guanine-cytosine (GC) or adenine-uracil, and deriving from the fitting a quantification of an amount of DNA and/or RNA. Receiving UV-VIS spectrophotometer data may comprise obtaining pre-stored UV-VIS spectrophotometer data or measuring UV-VIS spectrophotometer data for the one or more samples comprising DNA and/or RNA. Such UV-VIS spectrophotometer data typically may be a spectrophotometer spectrum, although information at one or more individual wavelengths or wavelength ranges also may be used. The sample comprising DNA and/or RNA may comprise single stranded DNA, double stranded DNA (dsDNA) and/or RNA.

Figure 4:
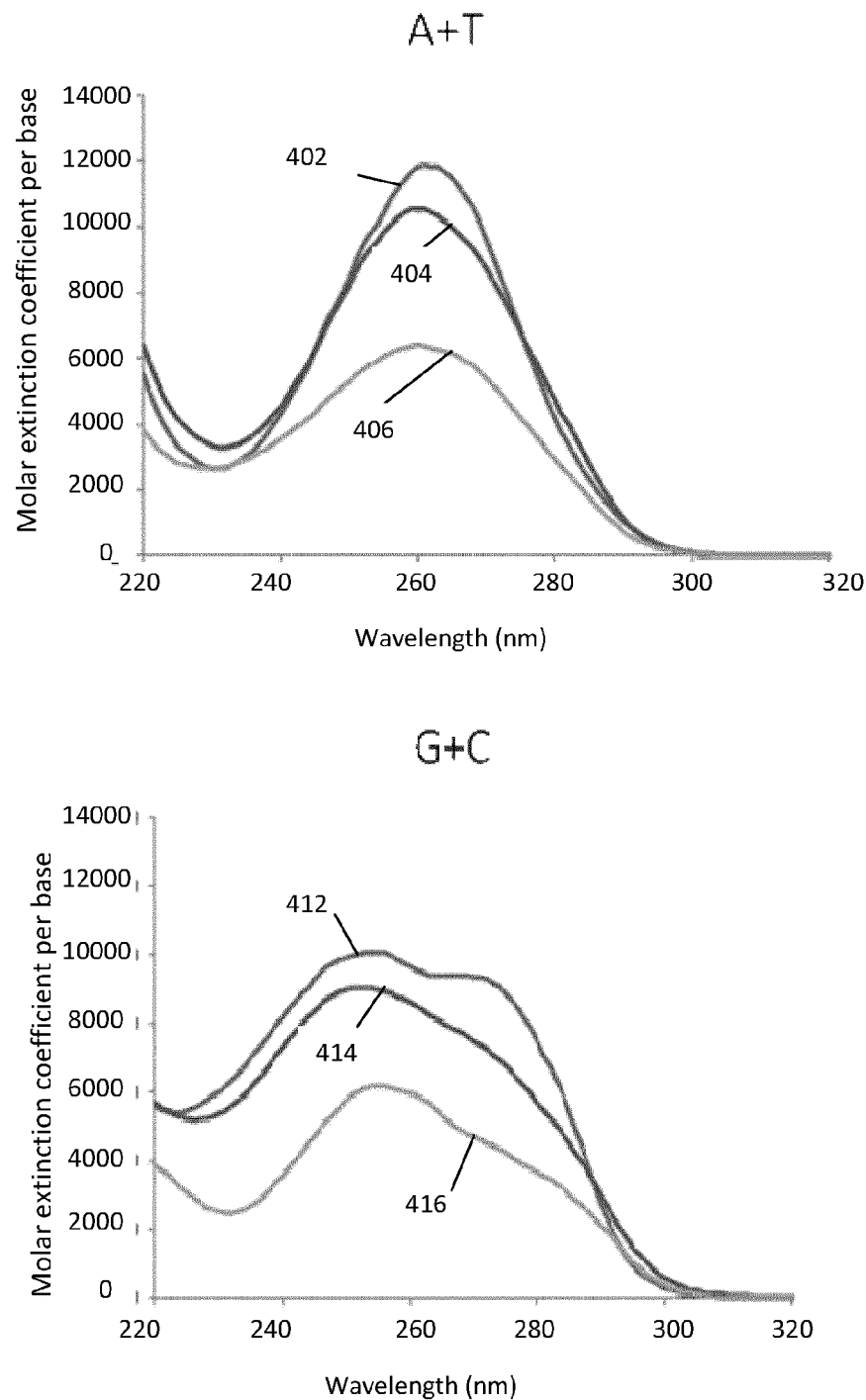
FIG. 4 illustrates the different spectral shapes for free nucleotides, nucleotides in single stranded DNA and double stranded DNA for adenine and thymine (top graph) and for guanine and cytosine (bottom graph), as can be used according to embodiments of the present invention.
Figure 5A:
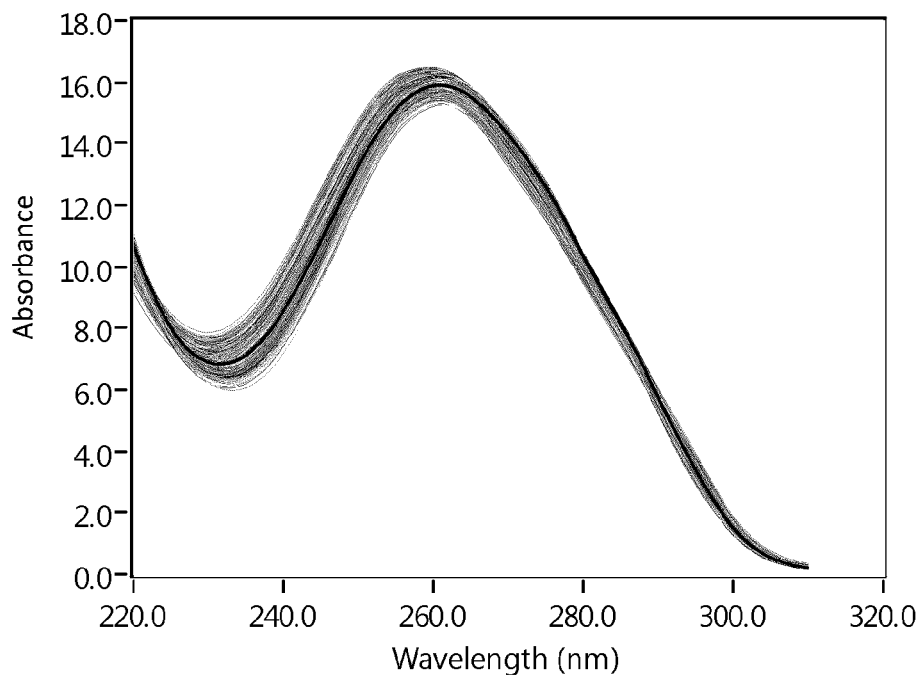
FIG. 5a to FIG. 5f illustrates simulation results illustrating the spectral variation for different lengths of base pair strands as function of the GC content, as can be used according to embodiments of the present invention.
Figure 5B:
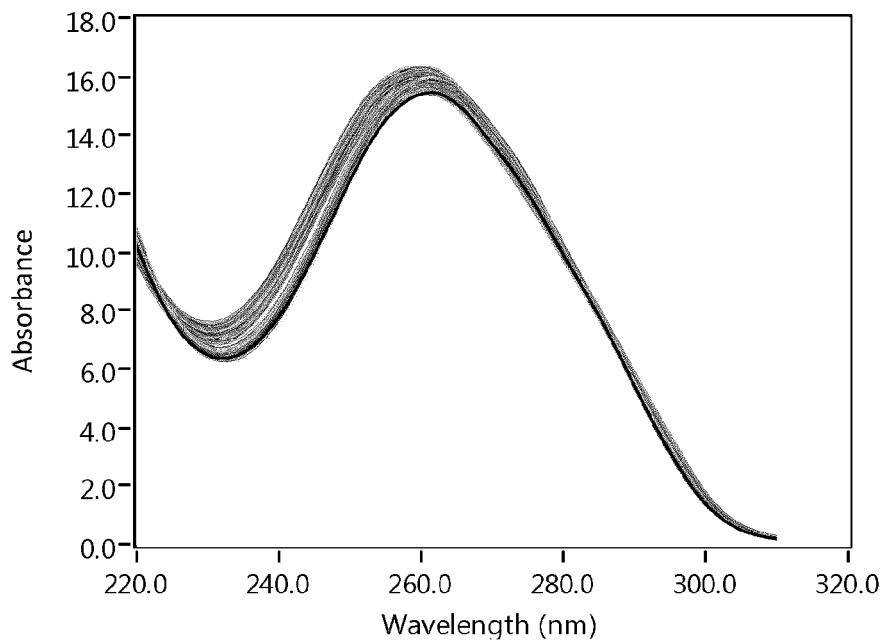
Figure 5C:
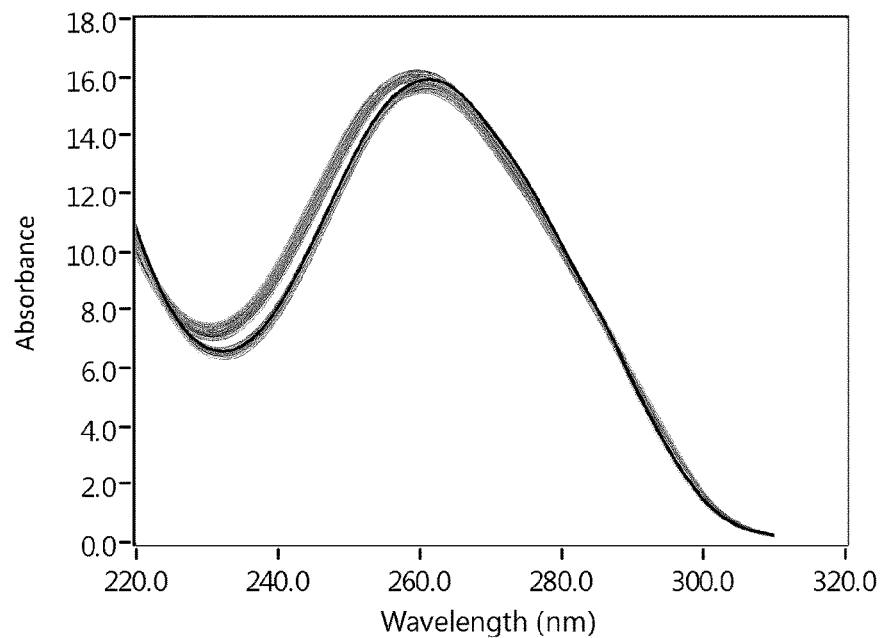
Figure 5D:
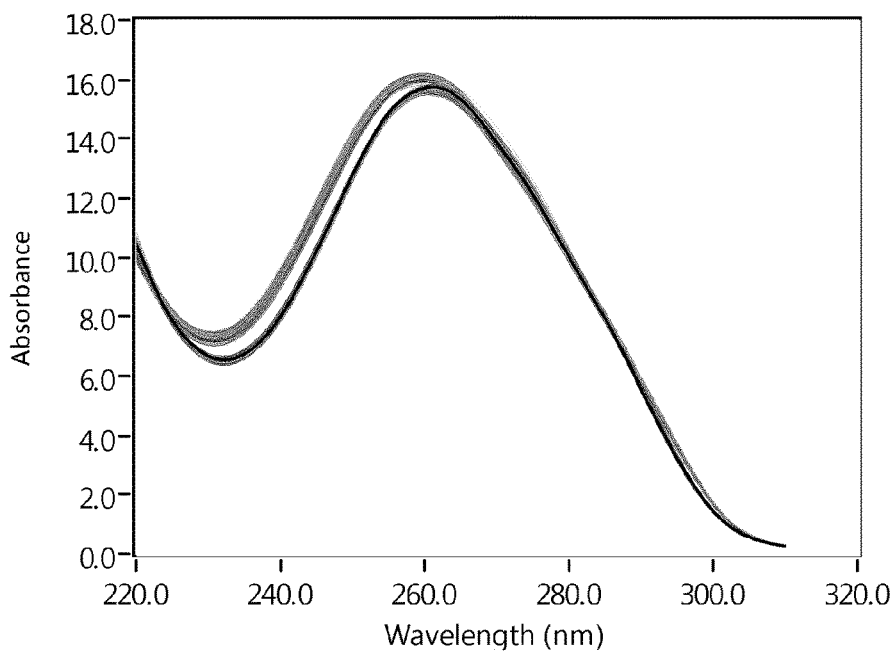
Figure 5E:
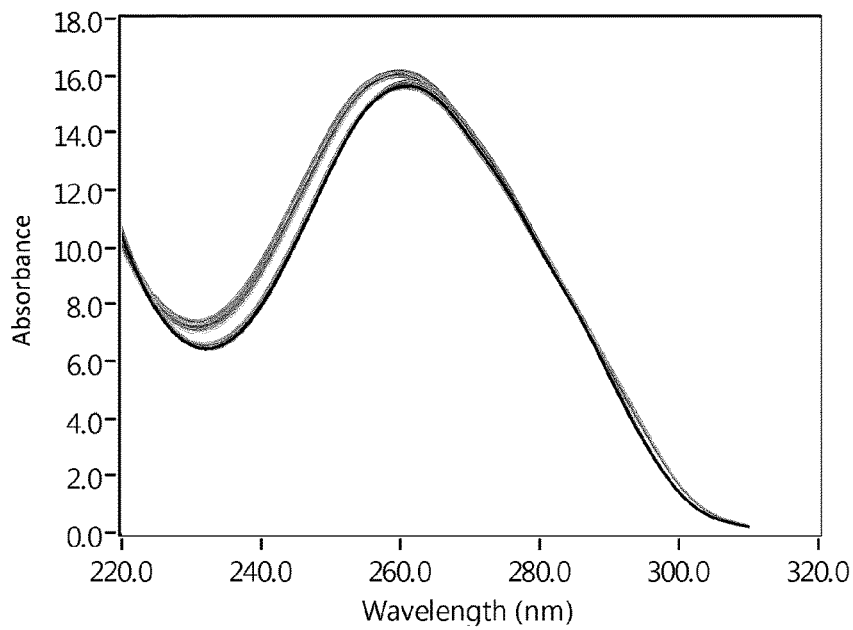
Figure 5F:
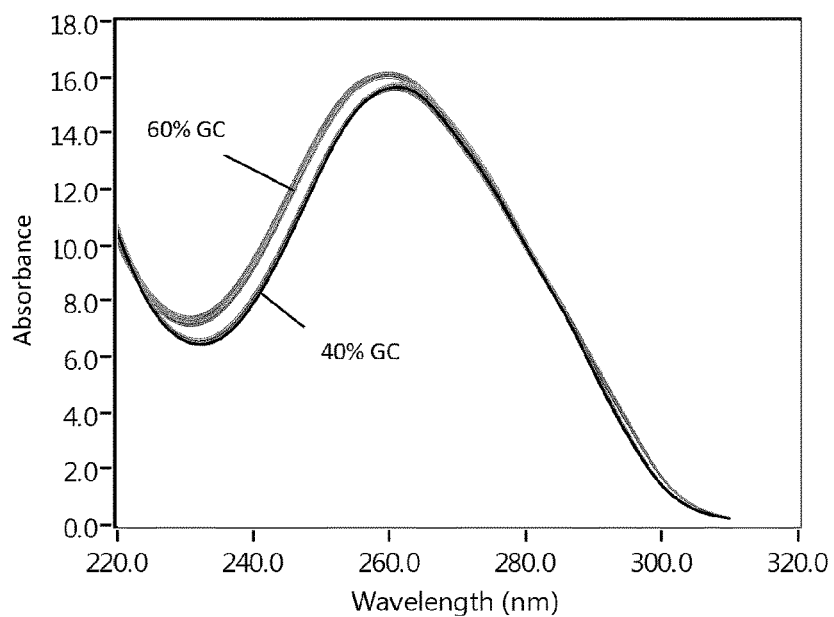

According to embodiments of the present invention, one step of the method comprises fitting the UV-VIS spectrometer data taking into account at least one spectrum representative for a base pair being any of adenine-thymine (AT) or guanine-cytosine (GC) or adenine-uracil. In some embodiments according to the present invention exactly two spectra representative for a base pair being any of adenine-thymine (AT) or guanine-cytosine (GC) or adenine-uracil are used. More particularly, in some embodiments use will be made of two reference spectra representative for samples having distinct GC contents. In other exemplary embodiments, such spectral components are used in combination with other spectra, or are combined with other spectra so that new spectra are obtained that can be used for the fitting. An example of different spectral forms wherein the nucleotides adenine, thymine, guanine and cytosine can occur is shown in FIG. 4, illustrating the occurrence from adenine and thymine on the one hand (drawing at top) and of guanine and cytosine on the other hand (drawing at bottom) as respectively a combination of free nucleotides (A+T curve 402; G+C curve 412), as occurring in single stranded DNA (A+T curve 404; G+C curve 414) and occurring as base pairs in double stranded DNA (A+T curve 406; G+C curve 416). The different spectral shapes can clearly be identified. Where in embodiments according to the present invention reference is made to a spectrum representative for a base pair, reference is made to the spectrum where nucleotides occur as base pairs in double stranded DNA or to a spectrum comprising spectral features for the situation where nucleotides occur as base pairs in double stranded DNA.

The method according to embodiments of the present invention also comprises deriving from the fitting a quantification of an amount of DNA and/or RNA. Deriving a quantification of an amount of DNA and/or RNA may for example comprise deriving an amount of single stranded DNA, an amount of double stranded DNA and or an amount of RNA. Embodiments of the present invention may be adapted for determining an amount of double stranded DNA, and deriving therefrom an amount of single stranded DNA or an amount of RNA.

By way of illustration, embodiments of the present invention not being limited thereto, a number of particular embodiments will further be described below.

In a first set of particular embodiments according to the present invention, a computer-implemented method as described above is disclosed, whereby fitting of UV-VIS spectrophotometer data of a sample comprising DNA and/or RNA comprises fitting the UV-VIS spectrophotometer data using exactly two reference spectra representative for base pairs. In the present embodiment, these two reference spectra are spectra representative for two samples having distinct particular base pair content, such as for example GC content. Typically, in such embodiments one reference spectrum will be representative of a sample having a higher GC content, whereas the other reference spectrum will be representative of a sample having a lower GC content. Where reference is made to distinct GC contents, the difference in content may be for example at least 20%, advantageously at least 30%, more advantageously at least 40%, e.g. at least 50%. Such embodiments may be especially suitable for fitting samples comprising DNA and/or RNA strands having at least 50 base pairs, advantageously at least 100 base pairs. Efficient fitting thus can be obtained. The latter is based on the surprising observation that the spectral variation for DNA with randomly generated sequences having a sufficient length can be fully explained taking into account the GC content, and can be accurately fit using two spectra representative for samples having distinct GC content.

In particular embodiments according to the present invention, a method for analyzing a polymerase chain reaction (PCR) based on the above described computer-implemented method is disclosed. For a PCR reaction, typically one starts from a mixture comprising deoxynucleotide Triphosphates, primer-oligo's, polymerase and a certain amount of DNA. The dNTP's in the mixture typically have a high optical density at 260 nm obscuring the contribution of the primers, target and amplicon, thus rendering it difficult to analyse such samples with respect to specific discrimination between the different components. Using embodiments according to the present invention will allow to evaluate and/or analyse the PCR reaction, even without purifying the reaction mixture, i.e. without separating components in the reaction mixture. Using embodiments according to the present invention, the amount of double stranded DNA that is formed, which is typically relatively small, can be accurately quantified, as well as the loss of deoxyribonucleotide triphosphate (dNTP). The formed amplicon can differ substantially in GC content, dependent on the final sequence. The varying shape of the double stranded DNA spectrum, being dependent on the GC content as indicated above, can be fitted using embodiments of the present invention as illustrated in the current description. Furthermore, in some embodiments, also the shape dependency on the mixture of free dNTP's can be taken into account. This shape dependency can e.g. be caused by the degree of consumption or incorporation of A+T and G+C nucleotides.

In a second set of particular embodiments, a method for analyzing a polymerase chain reaction (PCR) is described, wherein for fitting two reference spectra are used for distinct samples having distinct base pair content, such as for example distinct GC content, in combination with reference spectra for separate nucleobases. The latter reference spectra can for example be reference spectra for respectively A&T and G&C components, being combinations of individual spectra for nucleobases and not being the spectrum of dinucleotides. By making use of these reference spectra an appropriate fit can be obtained. Additionally also other components can be taken into account for the fitting, such as for example a component for scattering or turbidity, a component for a contamination such as for example for one or more of trimethylglycine, guanidinethiocyanate, phenol, ethylenediaminetetraacetic acid, proteins or hemoglobin, etc.

In a third set of particular embodiments, a method for analyzing a polymerase chain reaction (PCR) is described, wherein for fitting use is made of a spectrum of the sample before PCR action has taken place and two reference spectra being difference spectra expressing the incorporation of nucleobases, e.g. A&T and G&C nucleotides. Such difference spectra are obtained as the difference of the base pair spectrum of base pairs, e.g. AT respectively GC in a double stranded molecule, on the one hand and the spectrum obtained for separate nucleobases, e.g. nucleotide mixtures of A&T respectively G&C on the other hand.

By way of illustration, embodiments of the present invention not being limited thereby, simulation results are provided, illustrating how the above described deconvolution techniques can advantageously be used for analyzing samples comprising DNA.

A first set of simulation results illustrates that for long double stranded DNA, all spectral differences can be explained using two spectral components, e.g. an AT spectral component and a GC spectral component. The set of simulation results comprises fitting for double stranded DNA molecules with sizes ranging from 10 base pairs to 500 base pairs, with increments of 10 base pairs. The GC content for these particles ranges from 20% to 80% with increments of 10%. For each class of samples, 200 random sequences were generated.

Thereafter a prediction of the absorption spectra was made for all sequences using a method as described in "Predicting ultraviolet spectrum of single stranded and double stranded deoxyribonucleic acids", Biophysical Chemistry 133 (2008) 66-70 by Tataurov et al. The different spectra are shown in FIG. 5 for a selection of different lengths of the double stranded DNA. FIG. 5(a), 5(b), 5(c), 5(d), 5(e), 5(f) illustrate spectra for dsDNA having a length of respectively 10, 20, 50, 100, 200 and 500 base pairs.

For each class, the spread of the 200 spectra in each class was studied and it was identified whether or not a dependency as function of different GC content could be seen. It can be seen that for short double stranded DNA molecules, a large variation is present. No clear dependency of the GC content can be derived for the short double stranded DNA molecules, and it is concluded that the effect of the GC content is obscured by variation of the nearest-neighbour content. On the contrary, for the long double stranded DNA molecules, the variance in spectral shape for the 200 spectra in each class can mainly be explained by variance in GC content. In other words, the variance in spectral shape can substantially be explained by a single variable, being the GC content. By way of illustration, for double stranded DNA with a length of 500 base pairs, the possibility for fitting all these different spectra with one of two reference spectra having a particular GC content (one with high GC content and one with low GC content) is illustrated.

Figure 6:
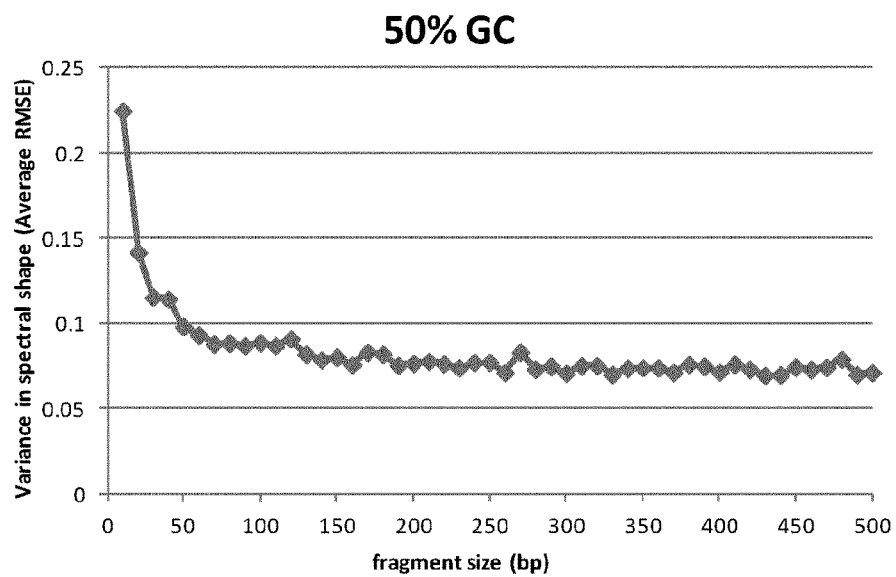
FIG. 6 is another illustration of the spectral variation as function of the length of strands of base pairs, as can be used according to embodiments of the present invention.
Figure 7A:
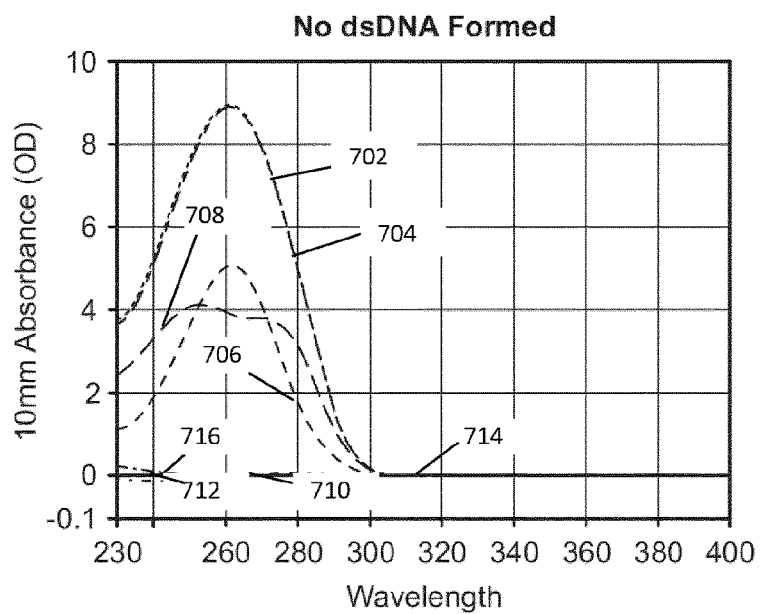
FIG. 7a, FIG. 7b, FIG. 8a and FIG. 8b illustrate measurement results obtained with different fitting techniques for distinguishing between a sample comprising double stranded DNA and a sample not comprising double stranded DNA, as can be used in embodiments of the present invention.
Figure 7B:
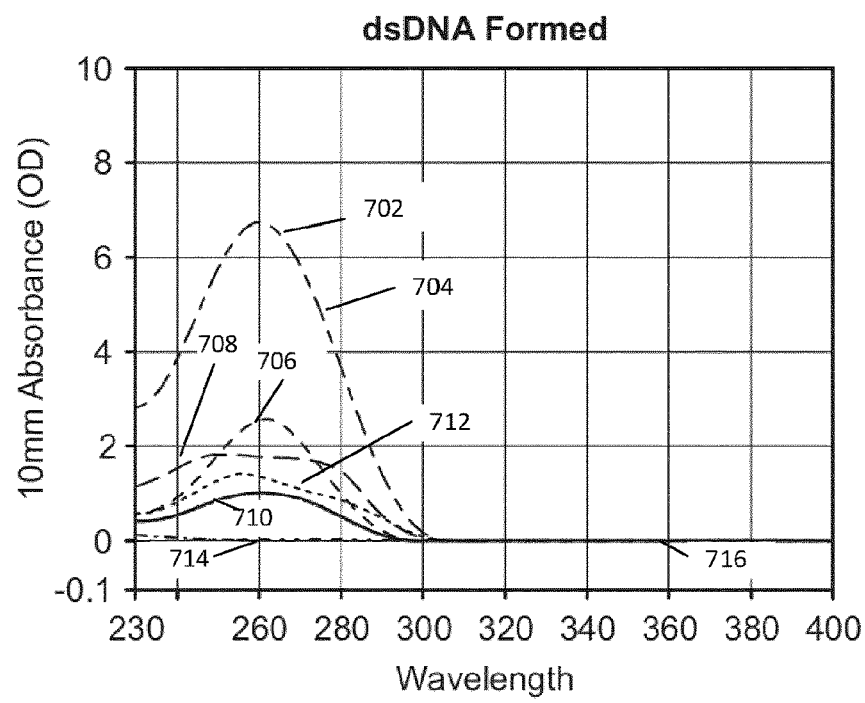

FIG. 6 illustrates for a given GC content (in the present case being 50% of GC content), the variance in spectral shape between different spectra as function of the fragment size of the double stranded DNA. It can be seen that the variance is large for fragment sizes between 1 and 50 base pairs. For fragment sizes of 50 base pairs or larger, e.g. 100 base pairs or larger, the variance in spectral shape is substantially lower, again indicative of the fact that for longer fragment sizes (although randomly generated), the spectral shape of the absorption spectrum is characteristic for a given GC content. By way of illustration, embodiments of the present invention not being limited thereby, an example of the application of an analysis method for analyzing a PCR measurement according to an embodiment of the present invention is discussed below with reference to FIG. 7a and FIG. 7b. FIG. 7a illustrates the output for analysis of an absorption spectrum of a sample whereby no double stranded DNA is formed and FIG. 7b illustrates the output for analysis of an absorption spectrum of a sample where double stranded DNA is formed. Although samples where PCR is used typically have a high optical density, the spectra still can be analysed, as shown in FIG. 7a and FIG. 7b.

The deconvolution method used is based on the use of two reference spectra for different GC concentrations (representative for basepairs; referred to as dsDNA_AT or A=T and dsDNA_GT or GC), e.g. extreme GC concentrations, and using two reference spectra for respectively A&T and G&C components (being combinations of individual spectra and not being the spectrum of dinucleotides; referred to as dNTPs_AT and dNTPs_GC). By making use of these reference spectra, in the present example, also taking into account other components such as for example a component for turbidity, an appropriate fit can be obtained, and it can indeed be distinguished whether or not double stranded DNA is formed by a PCR reaction. From the fitted concentrations of AT and GC double stranded DNA content, a quantification also can be performed. The measured spectrum 702 and the best fitted spectrum 704 coincide substantially. The dNTPS_AT component 706 and the DNTPS_GC component 708 are also indicated as well as the dsDNA_AT component 710, the dsDNA GC component 712, a residue component 714 and a component of other known contributing components 716. The last four are nearly not contributing.

Figure 8A:
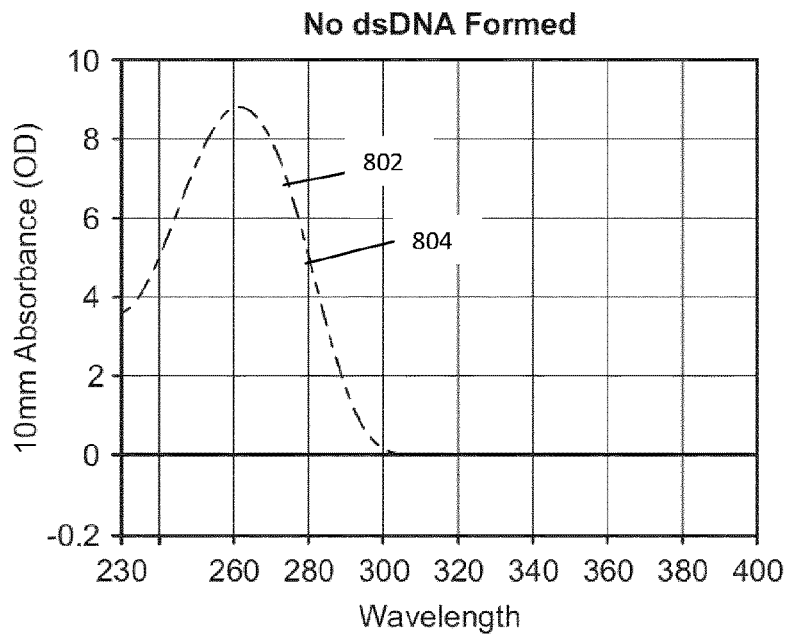
Figure 8B:
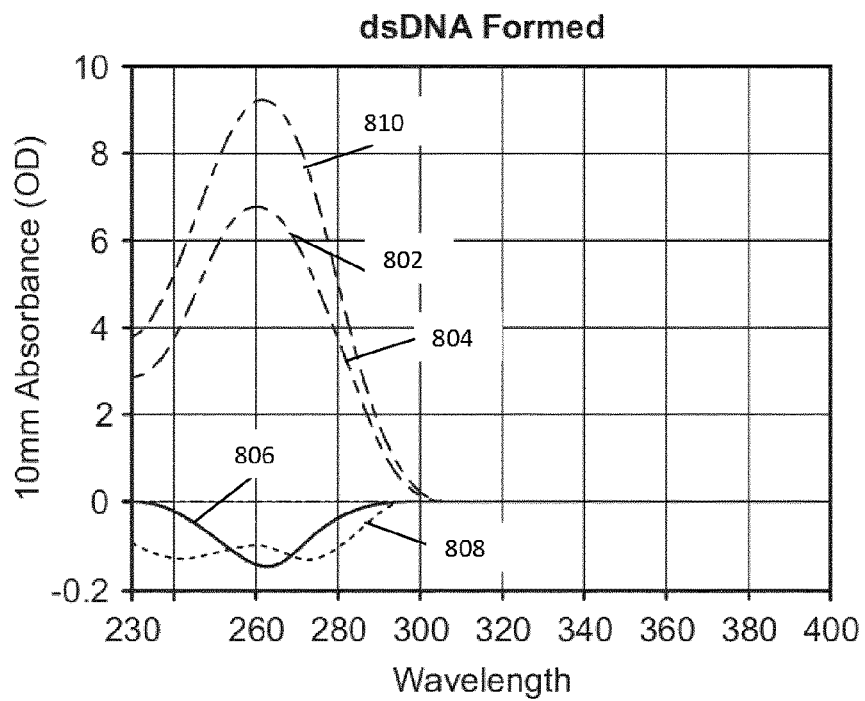

By way of illustration, embodiments of the present invention not being limited thereby, another example of the application of an analysis method for analyzing a PCR measurement according to an embodiment of the present invention is discussed below with reference to FIG. 8a and FIG. 8b. FIG. 8a and FIG. 8b illustrate the output for analysis of an absorption spectrum of a sample whereby no double stranded DNA is formed (FIG. 8a) and a sample where double stranded DNA is formed (FIG. 8b). Although samples where PCR is used typically have a high optical density, the spectra still can be analysed, as shown in FIG. 8a and FIG. 8b.

The deconvolution method used is based on the use of a spectrum of the sample before PCR action has taken place (Referred to as PCR mix) and two reference spectra being difference spectra expressing the building in of A&T and G&C. Such difference spectra for AT and GC are obtained as the difference of the spectrum obtained for separate nucleotide mixtures of AT respectively GC and the basepair spectrum of AT respectively GC in a double stranded configuration, i.e. as basepair. The measured spectrum 802 and the best fitted spectrum 804 are shown. For FIG. 8a, the other components and residue are substantially equal to 0. For FIG. 8b, furthermore the AT incorporation component 806, the GC incorporation component 808 and a PCR mix component 810 are also indicated. The other components and residue are substantially equal to 0.

By making use of these reference spectra, in the present example, optionally also taking into account other components such as for example a component for turbidity, an appropriate fit can be obtained, and it can indeed be distinguished whether or not double stranded DNA is formed by a PCR reaction. From the fitted concentrations of AT and GC double stranded DNA content, a quantification also can be performed. It is an advantage of embodiments according to the present invention that the result of the fit is a measure for the formed double stranded DNA and therefore allows a better quantification of the PCR reaction, than in the case of a method providing as end result the combination of the original double stranded DNA and the formed amplicons. It is furthermore an advantage of embodiments according to the present invention that automatically the AT and GC content balance is taken into account.

The above embodiments illustrate that by using deconvolution methods that taking into account the GC spectrum allows proper analysis of double stranded DNA and further even allows analysis of PCR reactions.

Figure 9:
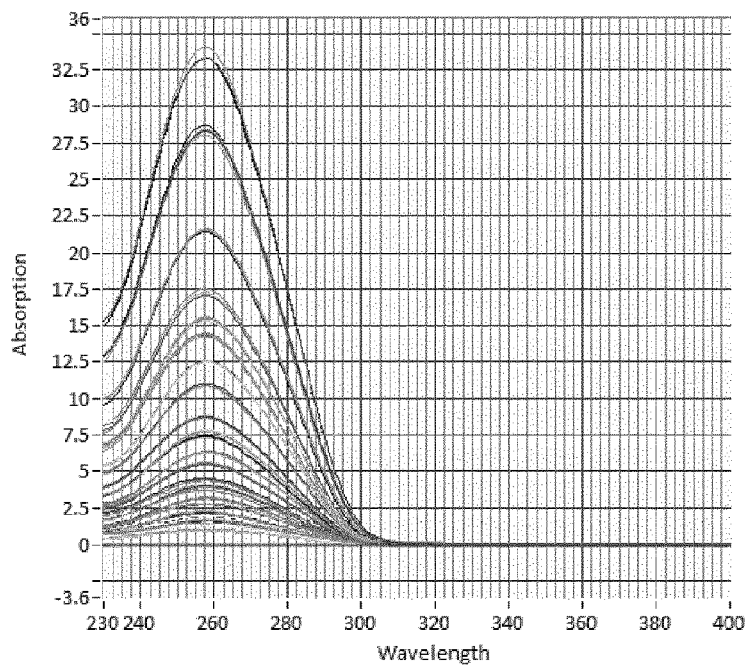
FIG. 9 illustrates spectroscopic spectra of mixed RNA and DNA, as can be analysed using methods according to embodiments of the present invention.

By way of illustration, embodiments of the present invention not being limited thereby, another example of the application of an analysis method for analyzing a sample comprising DNA and RNA according to an embodiment of the present invention is discussed below with reference to FIG. 9. FIG. 9 illustrates a set of samples comprising samples with different DNA to RNA ratios. The DNA/RNA ratios varied from 4:1 to 1:4. It can be seen that the spectral contributions of DNA and RNA significantly overlap. When the set of samples with the predetermined DNA/RNA ratios are deconvoluted using methods according to embodiments of the present invention, DNA/RNA ratios corresponding with the predetermined DNA/RNA ratios are found within experimental error, illustrating features and advantages of methods according to embodiments of the present invention.

Figure 10:
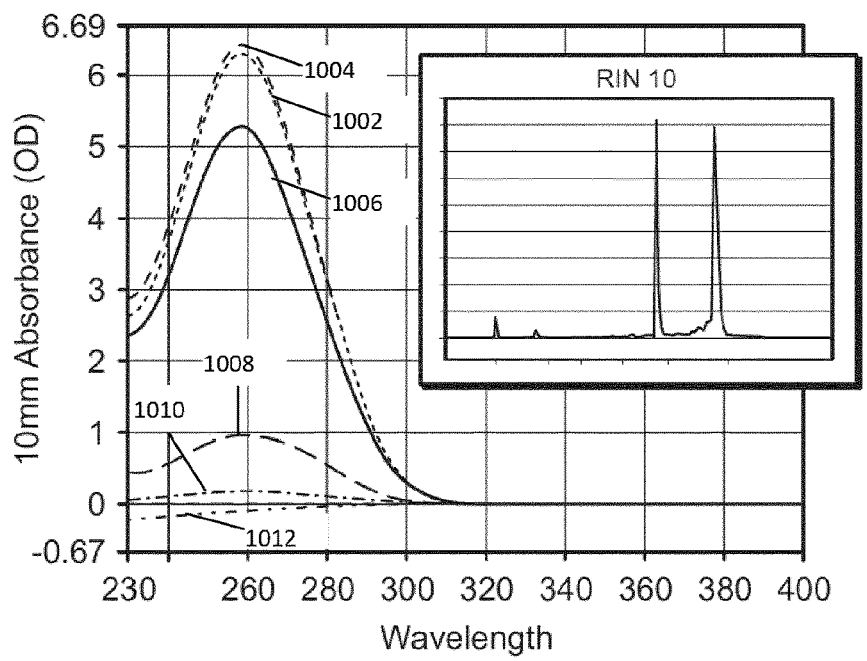
FIG. 10 to FIG. 11 illustrate deconvolution examples of two samples comprising RNA, analysed using methods according to embodiments of the present invention.
Figure 11:
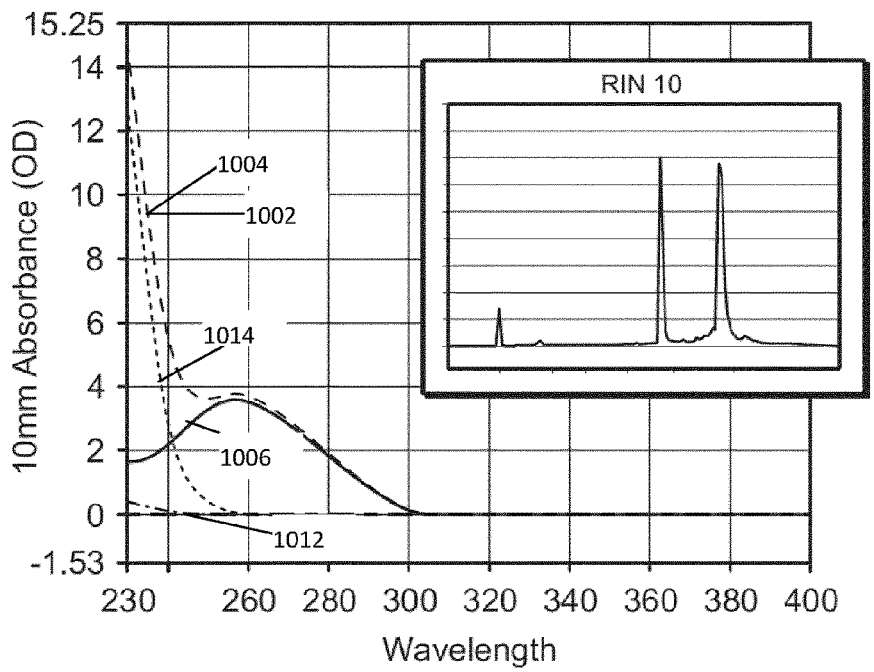

Further by way of illustration, the deconvolution of two RNA comprising samples is illustrated in FIGS. 10 and 11. FIG. 10 illustrates the deconvolution of a sample comprising both RNA, RNA nucleotides and DNA, whereby the measured spectrum 1002 is indicated, the best fit 1004 is indicated, the RNA component 1006 is indicated, the DNA component 1008 is indicated, an RNA nucleotides component 1010 is indicated, as well as a residue fraction 10012 is indicated. It could be seen that the residue fraction is smaller than 3%, indicative of the fit being accurate. The inset illustrates alternative measurement results based on electrophoretic separation and fluorescence analysis and confirms the presence of RNA (the RIN score of 10 corresponding with high integrity of RNA), as detected using the deconvolution technique according to an embodiment of the present invention. FIG. 11 illustrates the deconvolution of another sample comprising RNA, whereby the measured spectrum 1002 is indicated, the best fit 1004 is indicated, the RNA component 1006 is indicated, a Guanidinium thiocyanate component is also indicated, labeled as Guanidinium component 1014, and the residue 10012 also is indicated. The fraction of DNA and Protein is negligible. It could be seen that the residue fraction is only 0.83%, being indicative of a sufficiently good fit. The inset illustrates alternative measurement results based on electrophoretic separation and fluorescence analysis and confirms the quality of the sample RNA (the RIN score of 10) corresponding with high integrity of RNA, as detected using the deconvolution technique according to an embodiment of the present invention.

Embodiments of the present invention furthermore may be part of, may correspond with, may comprise one or more steps or features of or may make use of one or more of the following aspects, also being embodiments of the present invention.

By way of illustration, an exemplary flow chart of a method according to an embodiment of the present invention, comprising standard and optional steps is shown in FIG. 1, and will be further described with reference thereto below.

The method 100 according to embodiments of the present invention comprises obtaining 110 prior information for the one or more samples regarding their constituents. Such prior information for the one or more samples regarding their constituents may comprise in some embodiments one or more reference spectra. Such prior information alternatively or in addition thereto also may comprise expected composition information, such as for example expected concentrations, expected ratios between different constituents, etc. One example of such composition information may for example be the presence of a known polynucleotide, whereby the known polynucleotide is a known sequence of nucleotides such that known ratios of constituents, in the present example being nucleotides, are available. In some embodiments the prior information may be obtained based on the samples under study. In some embodiments the prior information may be previously stored information, such as for example previously stored reference spectra for constituents. In some embodiments a combination of such prior information also can be used.

The method also comprises obtaining 120 UV-VIS spectrophotometer data for the one or more samples. Such UV-VIS spectrophotometer data typically may be a spectrophotometer spectrum, although information at one or more individual wavelengths or wavelength ranges also may be used.

The method according to the present invention also comprises defining 130 a number of overlapping components contributing in the UV-VIS spectrophotometer data, the number of overlapping components comprising one or more components assigned to known constituents of the one or more samples and the number of components comprising one or more components that cannot be assigned to known constituents of the one or more samples. The components according to embodiments of the present invention expressing the contribution to the UV-VIS spectrophotometer data may in some embodiments comprise a spectral contribution with a shape differing from a Gaussian, Lorentzian or a mixture thereof. The shape of the spectral contribution may be a more broad contribution. Such one or more components that cannot be assigned to known constituents of the one or more samples may be as described above, such as for example modified constituents, neighboring effects between two constituents or contaminants. Defining the number of overlapping components may be based on a predetermined algorithm, a neural network, etc. The method may make use of a component analysis for defining the number of overlapping components, such as for example using a principal component analysis technique. In some embodiments the number of independent components can be obtained by putting a large number of absorbance spectra of the sample into a matrix and calculating a rank of the matrix.

The method according to the present invention furthermore comprises, using the prior information for the one or more samples regarding their constituents and using the UV-VIS spectrophotometer data, estimating 140 the constituents composition and the component contributions to the UV-VIS spectrophotometer data for the number of components for the one or more samples by minimizing a residue between the UV-VIS spectrophotometer data and a fit based on said constituent composition and said component contributions. For minimizing a residue different techniques may be employed such as for example a least square method, iterative error minimization, error entropy minimization, weighted error minimization, . . . .

In some embodiments, the prior information comprises reference contributions in the UV-VIS spectrophotometer data, such as for example reference spectra, for components assigned to known constituents. Estimating the constituents composition and the component contributions then may comprise estimating the component contributions to the UV-VIS spectrophotometer data for all components based on the reference contributions. Based on the component contributions, an estimate of the constituent composition is then determined based on the minimization of the residue between the UV-VIS spectrophotometer and the fit based on the estimated component contributions to the UV-VIS spectrophotometer data for all components.

In some embodiments, the prior information comprises constituent composition information for the one or more samples for the known constituents. Estimating the constituents composition and the component contributions then comprises estimating the constituent composition for all constituents based on the prior information on the constituent composition information for the one or more samples for the known constituents, and determining an estimate for the component contribution to the UV-VIS spectrophotometer data based on minimization of the residue between the UV-VIS spectrophotometer data and the fit based on said estimated constituent composition for all constituents.

In some embodiments a mixture of prior information is obtained, whereby the mixture of information allows for determining an estimate of the constituents composition and the component contributions.

The constituent composition and the component contributions may be interrelated by a model defining weighing factors for component distributions as function of the constituent composition. Such weighing factors may be taken into account when determining an estimate for the constituent composition or the component contribution.

The method also may comprise repeating 150 the estimating step and fitting step for further minimizing the total residue by iteratively applying these steps. Such iteration process may be performed until the remaining residue between the UV-VIS spectrophotometer data and the fit based on the constituent composition is smaller than a predetermined value, or until a maximum number of iteration steps would be reached. The predetermined value referred to may be based on predetermined rules, based on a neural network, based on predetermined algorithms, based on information regarding the one or more samples, etc. In some embodiments, minimization of the residue may only be performed for those samples that have the smallest residue, allowing obtaining more accurate results and/or quicker convergence.

The method allows providing as an output information regarding the composition of the sample and/or information regarding the spectral contribution of constituents to the absorbance spectra. In some examples, the obtained information may allow deriving a reference spectra for a constituent, a modified constituent, a contaminant, a neighbouring effect, . . . . The latter can be used for setting up a library of different reference spectra compatible with different constituents or effects thereof.

In one embodiments, the method also comprises using the residue of each sample or information related thereto to check the available a priori information. In other words, the results obtained using the method can be used for cross-checking the available a priori information.

The method according to embodiments of the present invention may especially be suitable for analyzing a plurality of samples, whereby in one part of the samples the unknown component is present and in another part of the samples the unknown component is absent.

The method according to embodiments of the present invention may be implemented as software as well as hardware.

Figure 2:
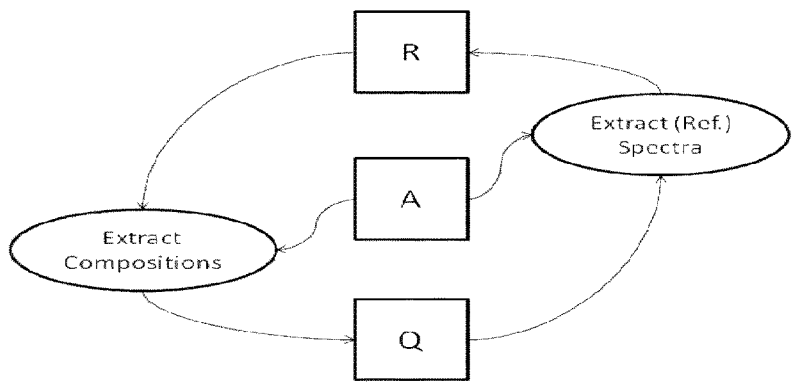
FIG. 2 illustrates an example of data flow as can be obtained using embodiments of the present invention.
Figure 3:
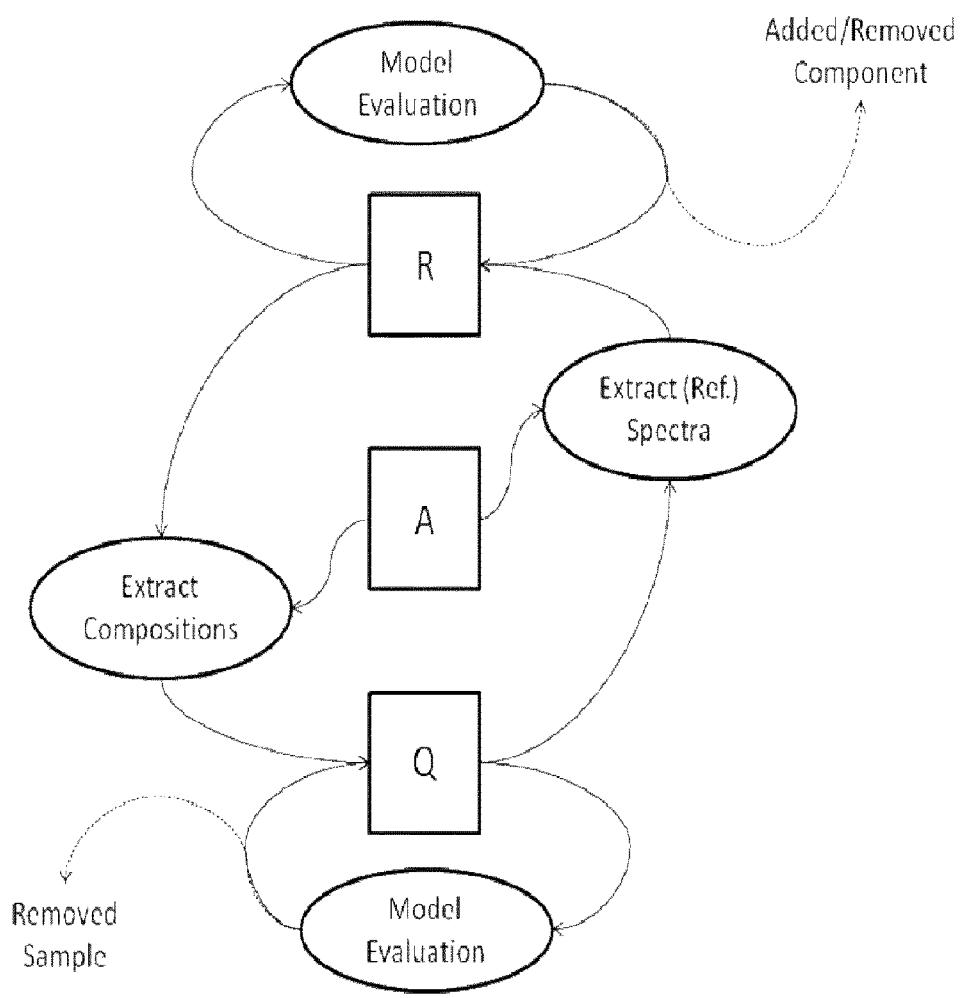
FIG. 3 illustrates an example of data flow as can be obtained using embodiments of the present invention.

By way of illustration, embodiments of the present invention not being limited thereto, an example of how data can be combined and obtained is illustrated in FIG. 2. FIG. 2 illustrates how, according to embodiments of the present invention, based on spectrophotometer data and composition information (e.g. obtained based on prior knowledge), component contributions can be determined, e.g. in the shape of reference spectra by minimizing the residue. Based on the obtained component contributions and using the spectrophotometer data, improved estimates of the composition can be obtained. FIG. 3 illustrates a further embodiment of the present invention, whereby upon estimation of the composition information or the component contribution information, it can be decided to add an additional component or remove a component by evaluating the component contribution data obtained e.g. in the light of the expected results in view of the prior data, or it can be decided to remove a sample in the evaluation based on an evaluation of the composition information obtained e.g. in the light of the expected results in view of the prior data.

The method may be suitable for extracting quantitative information about one or more constituents in the sample and the corresponding component contribution in the UV-VIS spectrum. In some embodiments, corresponding reference spectra of known and unknown components suspected to the present in the sample, can be used for fitting the UV-VIS spectrophotometer data. The component contributions may not be limited to the reference spectra of the individual pure components, but may be extended with corrective spectral functions of components that do not necessarily correspond to a physic-chemical absorption characteristic of the component, nor does the component itself needs to show significant absorption characteristics within the wavelength region under study. In one example, one of the component contributions may be a contribution corresponding with turbidity caused by concentration or aggregation effects. In one example, one of the component contributions may be a contribution corresponding with scatter caused by residual particles, e.g. particles present due to pre-processing of the sample.

By way of illustration, embodiments of the present invention not being limited thereto, an algorithm comprising a number of particular steps will be described illustrating an exemplary way of implementing the method according to embodiments of the present invention or that can be used in embodiments for fitting in methods for analyzing samples comprising DNA and/or RNA. The method will be described using a particular mathematical matrix formalism, although embodiments of the present invention are not limited thereto another mathematical formalism also may be used. The example illustrates the methods used for deconvolution of spectrophotometric data. The principles apply for different kinds of samples.

For illustrating the algorithm, a number of definitions first are provided:

$A_i$: this is a measurement (expressed in absorbances, OD10 mm) where the subscript I denotes the wavelengths (ranging from 220 nm to 360 nm in 1 nm steps, in case of nucleic acids)

$Q_j$: this matrix contains the relative presences of the different known and unknown constituents, interaction effects, modifications or contaminations of the mixture. In the present example these can be e.g. the nucleotides A, G, C and T but also modifications (like labels) or dinucleotides such as for example AG, because some dinucleotide spectra differ from the combined spectra of their constituents. In the current algorithm dinucleotides are treated identical to modifications and contaminants. j is the number of subcomponents in the mixture.

$R_{ij}$: the reference spectra. These are the (known) spectra of the nucleotides and the spectra of the modifications, dinucleotides and contaminants. With i the wavelengths and j the subcomponents.

When working with stored reference spectra, $R_j$, the coefficients of each reference spectrum, $Q_{ij}$, can be the unknown.

When measuring known components, $Q_{ij}$, is already specified and the reference spectra $R_j$ can be derived.

In reality, an iterative procedure will be used where in a first step, $R_j$ is determined and in subsequent steps $Q_{ij}$, is found and again and again.

The measurements, relative presences and contributions (in the present example being known reference spectra) are given as $$R_{ij}Q_j = A_i \text{ or } RQ = A \qquad [1]$$

The definitions in case a plurality of samples are measured result in the measurement matrix becoming $A_{ik}$: this is a measurement (expressed in absorbances, OD10 mm) where the subscript i denotes the wavelengths (ranging from 220 nm to 360 nm in 1 nm steps, in case of nucleic acids) and k the number of the measurements the coefficient matrix becoming $Q_{jk}$: this matrix contains the coefficients (the relative presences) of every subcomponent of the mixture. Here subcomponents can be the nucleotides A, G, C and T but also modifications (like labels) and dinucleotides (e.g. AG) and contaminants. Again j is the number of subcomponents, and k the number of measurements.

Resulting in the following equation expressing the relation between the components (in the present example known from prior info and being reference spectra R) the coefficient matrix (in the present example expressing the constituent composition) and the measurement matrix.

$$R_{ij}Q_{jk} = A_{ik} \text{ or } RQ = A \qquad [2]$$

In the present example, the available prior information corresponds with the reference spectra for the constituents in the sample. In such a case both the components contribution information R and the spectrophotometer data A in equation [2] are known. To determine the sample composition Q first left-multiply the equation with the component contribution information R transposed and then left-multiply both sides of the equation with the inverse of the matrix product of the component contribution R transposed and the component contribution R $$(R^T \cdot R)^{-1} \cdot R^T \cdot R \cdot Q = (R^T \cdot R)^{-1} \cdot R^T \cdot A \qquad [3]$$

$$Q = (R^T \cdot R)^{-1} \cdot R^T \cdot A = pinv(R) \cdot A \qquad [4]$$

This is in fact the equation for the matrix linear regression or linear least squares. The expression in the right side before the spectrophotometer data A is known as the pseudo-inverse of the matrix R and can be for example calculated using singular value decomposition.

By way of illustration, also an example for the inverse situation will be discussed, whereby constituents composition is known and whereby the reference spectra need to be determined.

Thus, the inverse problem where the coefficients of the subcomponents are known, the measurements are known and the aim is to obtain the reference spectra, is discussed below.

By transposing the entire equation [1] the following relation is obtained.

$$Q^T \cdot R^T = A^T \qquad [5]$$

and the reference spectra can be found by $$R^T = pinv(Q^T) \cdot A^T \qquad [6]$$

In the above two examples, the situation of known constituents is shown.

The above algorithm indicates features and advantages that can be obtained using a method as described in an embodiment of the present invention.

In one aspect, the present invention also relates to a system for analyzing UV-VIS spectrophotometer data of one or more samples comprising DNA and/or RNA, the system comprising an input means for receiving said UV-VIS spectrophotometer data, a processing means programmed for fitting the UV-VIS spectrometer data taking into account at least one spectrum representative for a base pair being any of adenine-thymine (AT) or guanine-cytosine (GC) or adenine-uracil, and deriving from the fitting a quantification of an amount of DNA and/or RNA, and an output means for outputting a quantification of an amount of DNA and/or RNA for the one or more samples under study. Further optional features and advantages may correspond with components for performing the functionality of the steps expressed in the methods described above. Furthermore, features and advantages of further systems or components thereof described below, also being aspects of the present invention, also may be partially or fully incorporated in systems for analyzing UV-VIS spectrophotometer data of one or more samples comprising DNA and/or RNA referred to above. Such further systems may be for example be a system for performing analysis of spectrophotometer data of one or more samples consisting of a number of constituents. The system comprises an input means for obtaining prior information for the one or more samples regarding their constituents and for obtaining UV-VIS spectrophotometer data for the one or more samples. The latter may be an input port for receiving prior information and spectrophotometer data. Alternatively the input means may also comprise a measurement system for recording UV-VIS spectrophotometer data such as for example a spectrophotometer.

The system furthermore comprises a processing means programmed for defining a number of overlapping components contributing in the UV-VIS spectrophotometer data, the number of components comprising one or more components assigned to known constituents of the one or more samples and the number of components comprising one or more components that cannot be assigned to known constituents of the one or more samples. Such a processing means may be for example a CPU although embodiments of the present invention are not limited thereto. The processing means according to embodiments of the present invention furthermore is programmed for using the prior information for the one or more samples regarding their constituents and using the UV-VIS spectrophotometer data, estimating the 10 constituents composition and the component contributions to the UV-VIS spectrophotometer data for the number of components for the one or more samples by minimizing a residue between the UV-VIS spectrophotometer data and a fit based on said constituent composition and said component contributions, thus obtaining information regarding the one or more components that cannot be assigned to known constituents of the one or more samples. Such information may be putted out using an outputting means, such as e.g. a memory, a display, a printer or a plotter.

In another aspect, the present invention relates to a method for extracting component contributions, e.g. reference spectra for particular constituents of the sample of for contributions of such constituents being modified, disturbed or being in a particular environment. The reference spectra can be extracted using methods as described above. Such a method for extracting component contributions may correspond with a method for analyzing UV-VIS spectrophotometer data of a sample comprising DNA and/or RNA as described above.

In one aspect, the present invention also relates to the use of a method as described above for particular applications. One of these applications may be identifying and/or quantifying contaminants in DNA or RNA samples. The contaminants may be protein contamination. The contaminants in one application may be PCR-inhibiting contaminants. Another application envisaged is the quantification of an amount of double-stranded DNA in a mixture of double-stranded DNA and single-stranded RNA or DNA. Still a further application is determination of the composition of a polynucleotide or protein. A further application is the quantification of the modification efficiency in a sample. The method also may be applied for validating a sample composition or a constituent thereof or group of constituents thereof. By extension the method allows to extract more detailed information about the composition of a component, in particular of polymers, and more specifically in biopolymers such as polynucleotides and proteins. Inversely, the method also allows to extract quantitative information of polymers based on the a priori knowledge of the composition of the known components, rather than the knowledge of the spectrum of the component.

In still another aspect, embodiments of the present invention also relate to computer-implemented methods for performing at least part of the methods for analyzing spectrophotometer data. Embodiments of the present invention also relate to corresponding computer program products. The methods may be implemented in a computing system. They may be implemented as software, as hardware or as a combination thereof. Such methods may be adapted for being performed on computer in an automated and/or automatic way. In case of implementation or partly implementation as software, such software may be adapted to run on suitable computer or computer platform, based on one or more processors. The software may be adapted for use with any suitable operating system such as for example a Windows operating system or Linux operating system. The computing means may comprise a processing means or processor for processing data. According to some embodiments, the processing means or processor may be adapted for analyzing spectra according to any of the methods as described above or extracting reference spectra according to any of the methods as described above. Besides a processor, the computing system furthermore may comprise a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. The obtained results may be outputted through an output means such as for example a plotter, printer, display or as output data in electronic format.

Further aspect of embodiments of the present invention encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

The invention claimed is:

1. A computer-implemented method for analyzing UV-VIS spectrophotometer data of a sample comprising DNA the method comprising:
   receiving UV-VIS spectrophotometer data of the sample;
   fitting the UV-VIS spectrophotometer data of the DNA in the sample according to instructions run by a processing unit, wherein fitting comprises taking into account a set of exactly two reference spectra representative of two distinct base pair contents, the base pair being guanine-cytosine (GC); and deriving from the fitting run by the processing unit a quantification of an amount of DNA.

2. The computer-implemented method according to claim 1, wherein said fitting comprises fitting UV-VIS spectrophotometer data of a sample comprising DNA and/or RNA having at least 50 base pairs, advantageously at least 100 base pairs.

3. The computer-implemented method according to claim 1, the sample comprising DNA,
   wherein said fitting comprises using a combination of a set of reference spectra representative for base pairs and reference spectra being representative for separate nucleobases.

4. The computer-implemented method according to claim 3, wherein said fitting using a combination of reference spectra representative for base pairs and reference spectra being representative for separate nucleobases comprises fitting using spectra being the difference spectra between reference spectra representative for base pairs and reference spectra being representative for separate nucleobases.

5. The computer-implemented method according to claim 4, wherein the difference spectra between reference spectra representative for base pairs and reference spectra being representative for separate nucleobases are spectra obtained by subtracting from a given reference spectra representative for a given base pair, the reference spectra being representative for the corresponding separate nucleobases.

6. The computer-implemented method according to claim 3, wherein the reference spectra representative of separate nucleobases are reference spectra for adenine, guanine, thymine, cytosine and/or uracil.

7. The computer-implemented method according to claim 1, the method being adapted for analyzing a PCR reaction of a sample comprising DNA,
   wherein said deriving comprises determining an amount of double stranded DNA formed during or after a PCR reaction.

8. The computer-implemented method according to claim 7, wherein fitting furthermore comprises taking into account a spectral component for a contamination component.

9. The computer-implemented method according to claim 8, wherein taking into account a spectral component for a contamination component comprises taking into account a spectral component for one or more of trimethylglycine, guanidinethiocyanate, phenol, ethylenediaminetetraacetic acid, proteins sodium azide or hemoglobine.

10. The computer-implemented method according to claim 7, wherein fitting UV-VIS spectrophotometer data of a sample comprises fitting UV-VIS spectrophotometer data of a mixture comprising deoxynucleotide Triphosphates, primer-oligo's, polymerase and DNA.

11. The computer-implemented method according to claim 1, wherein fitting furthermore comprises taking into account one or more spectral components representative for scattering in the sample and/or wherein fitting furthermore comprises taking into account one or more spectral components representative for turbidity in the sample.

12. The computer-implemented method according to claim 1, wherein the DNA is at least an amount of double stranded DNA.

13. The computer-implemented method according to claim 1, wherein the obtaining of the UV-VIS spectrophotometer data includes using a spectrophotometer.

14. The computer-implemented method according to claim 1, wherein the UV-VIS spectrophotometer data is obtained by irradiating the sample with UV-VIS radiation in the range from 300 nm to 1100 nm.

15. A computer-implemented system for analyzing UV-VIS spectrophotometer data of a sample comprising DNA, the system comprising:
   a spectrophotometer configured to obtain UV-VIS spectrophotometer data from the sample by irradiating the sample with UV-VIS radiation of different wavelengths and measuring a spectrophotometer from the sample, the spectrophotometer being further configured to output UV-VIS spectrophotometer data, and
   at least one or more processors configured to receive said UV-VIS spectrophotometer data and fit the UV-VIS spectrophotometer data according to instructions run by the at least one or more processors, wherein the fitting comprises taking into account a set of two or a set of exactly two reference spectra representative of two distinct base pair contents, the base pair being guanine-cytosine (GC), and the at least one or more processors being further configured to derive from the fitting a quantification of an amount of DNA or RNA, wherein the system is configured to output a quantification of an amount of DNA for the sample under study.

16. One or more non-transitory computer-readable storage media comprising instructions stored thereon that, responsive to execution by one or more computing devices, cause the one or more computing devices to implement a system to perform one or more operations comprising:
   obtaining UV-VIS spectrophotometer data from the sample by irradiating the sample with UV-VIS radiation of different wavelengths and measuring a spectrophotometer from the sample;
   outputting the UV-VIS spectrophotometer data to at least one or more processors;
   receiving the UV-VIS spectrophotometer data by the at least one or more processors;
   fitting the UV-VIS spectrometer data by the at least one or more processors by taking into account a set of two or a set of exactly two reference spectra representative of two distinct base pair contents, the base pair being;
   deriving by the at least one or more processors from the fitting a quantification of an amount of DNA and/or RNA within the sample; and
   outputting the quantification of the amount of the DNA and/or RNA.

17. The computer-implemented method according to claim 13, wherein the spectrophotometer is configured such that the UV-VIS spectrophotometer data obtained are absorbance data that is representative of the absorption that has occurred in the sample.

18. A computer-implemented method for analyzing UV-VIS spectrophotometer data of a sample comprising RNA, the method comprising:
   receiving UV-VIS spectrophotometer data of the sample;
   fitting the UV-VIS spectrophotometer data of the RNA in the sample according to instructions run by a processing unit, wherein fitting comprises taking into account a set of two or a set of exactly two reference spectra representative of two distinct base pair contents, the base pair being guanine-cytosine (GC); and
   deriving from the fitting a quantification of an amount of RNA.

* * * * *